(12) United States Patent
Nyren et al.

(10) Patent No.: US 6,210,891 B1
(45) Date of Patent: Apr. 3, 2001

(54) METHOD OF SEQUENCING DNA

(75) Inventors: Pål Nyren, Skarpnäack; Mathias Uhlen, Täby; Mostafa Ronaghi, Stockholm, all of (SE)

(73) Assignee: Pyrosequencing AB, Uppsala (SE)

( * ) Notice: Subject to any disclaimer, the term of this patent is extended or adjusted under 35 U.S.C. 154(b) by 0 days.

(21) Appl. No.: 09/269,436

(22) PCT Filed: Sep. 26, 1997

(86) PCT No.: PCT/GB97/02631

§ 371 Date: Jul. 6, 1999

§ 102(e) Date: Jul. 6, 1999

(87) PCT Pub. No.: WO98/13523

PCT Pub. Date: Apr. 2, 1998

(30) Foreign Application Priority Data

Sep. 27, 1996 (GB) .................................................. 9620209

(51) Int. Cl.[7] .............................. C12Q 1/68; C12Q 1/66; C12P 19/34; C07H 21/04
(52) U.S. Cl. ................................. 435/6; 435/8; 435/91.2; 435/91.21; 536/243; 536/24.33
(58) Field of Search .................. 435/6, 8, 91.2, 435/91.21; 536/24.3, 24.33

(56) References Cited

U.S. PATENT DOCUMENTS

| | | | |
|---|---|---|---|
| 4,851,331 | 7/1989 | Vary et al. | 435/6 |
| 4,863,849 | 9/1989 | Melamede | 435/6 |
| 4,971,903 | 11/1990 | Hyman | 435/6 |
| 5,302,509 | 4/1994 | Cheesemann | 435/6 |
| 5,405,746 | 4/1995 | Uhlen | 435/6 |
| 5,498,523 | 3/1996 | Tabor et al. | 435/6 |
| 5,534,407 | 7/1996 | Tabor et al. | 435/5 |
| 5,534,424 | 7/1996 | Uhlen et al. | 435/91.2 |
| 5,599,675 | 2/1997 | Brenner et al. | 435/6 |
| 5,665,545 * | 9/1997 | Malek et al. | 435/6 |
| 5,674,716 | 10/1997 | Tabor et al. | 435/91.1 |
| 5,679,524 | 10/1997 | Nikiforov et al. | 435/6 |
| 5,834,189 | 11/1998 | Stevens et al. | 435/6 |
| 5,849,487 | 12/1998 | Hase et al. | 435/6 |
| 5,856,092 | 1/1999 | Dale et al. | 435/6 |
| 5,888,819 | 3/1999 | Goelet et al. | 435/5 |

FOREIGN PATENT DOCUMENTS

| | | |
|---|---|---|
| WO 89/09283 | 10/1989 | (DE) . |
| 414178 | 6/1993 | (DE) . |
| 0223618 | 5/1987 | (EP) . |
| 0298669 | 1/1989 | (EP) . |
| 0412883 | 2/1991 | (EP) . |
| 0663447 | 7/1995 | (EP) . |

(List continued on next page.)

OTHER PUBLICATIONS

Sanger et al., "DNA sequencing with chain–terminating inhibitors", Proceedings of the National Academy of Sciences, USA, vol. 74 (12), pp. 5463–5467, Dec. 1977.*

Stratagene Catalog, p. 39, 1988.*

(List continued on next page.)

*Primary Examiner*—Jeffrey Fredman
*Assistant Examiner*—Arun Chakrabarti
(74) *Attorney, Agent, or Firm*—Baker Botts

(57) ABSTRACT

The present invention provides a method of identifying a base at a target position in a single-stranded sample DNA sequence wherein an extension primer, which hybridizes to the sample DNA immediately adjacent to the target position, is provided and the sample DNA and extension primer are subjected to a polymerization reaction in the presence of a deoxynucleotide or dideoxynucleotide, whereby the deoxynucleotide or dideoxynucleotide will only become incorporated and release pyrophosphate if it is complementary to the base in the target position. Release of pyrophosphate is detected enzymatically and pyrophosphate detection enzyme(s) are included in the polymerization step.

11 Claims, 7 Drawing Sheets

FOREIGN PATENT DOCUMENTS

Figure 1:
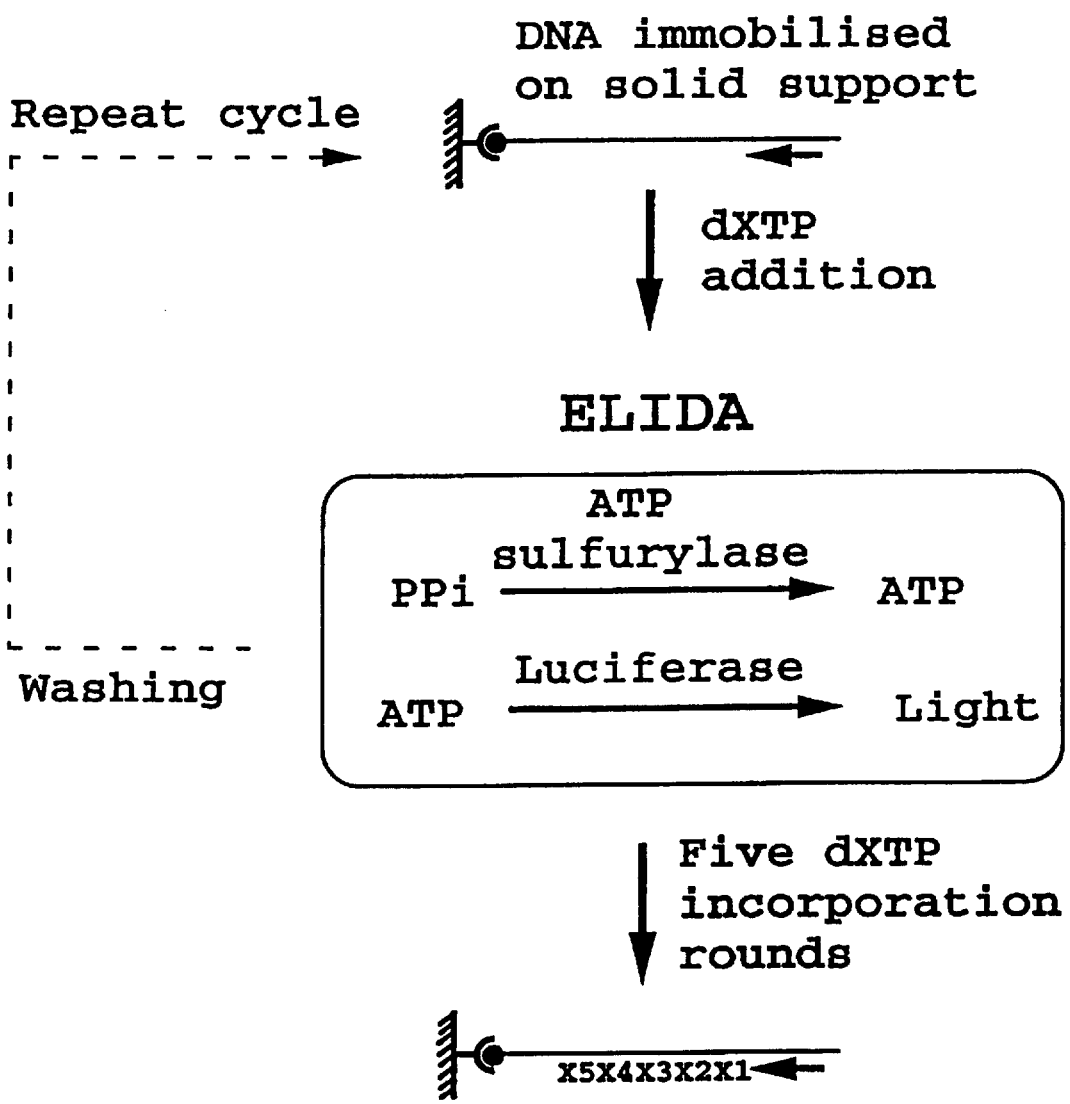

| | | |
|---|---|---|
| WO 89/12063 | 12/1989 | (WO). |
| WO 91/06678 | 5/1991 | (WO). |
| WO 91/13075 | 9/1991 | (WO). |
| WO 93/21340 | 10/1993 | (WO). |
| WO 93/233563 | 11/1993 | (WO). |
| WO 93/23562 | 11/1993 | (WO). |
| WO 93/23564 | 11/1993 | (WO). |
| 9417198 | 8/1994 | (WO). |

OTHER PUBLICATIONS

Benkovic et al. (1995) Methods in Emzymology 28:257.
Gupta et al. (1984) Nucleic Acids Research 12:5897.
Hultman et al. (1990) Nucleic Acids Research 18:5107.
Hyman (1988) Analytical Biochemistry 174:423.
Kajiyama et al. (1994) Biosci. Biotech. Biochem. 58:1170.
Nyren (1987) Analytical Biochemistry 167:235.
Nyren (1993) Analytical Biochemistry 208:171.
Nyren et al. (1985) Analytical Biochemistry 151:504.
Patel et al. (1991) Biochemistry 30:511.
Ronaghi et al. (1996) Analytical Biochemistry 242:84.
Syvanen et al. (1990) Genomics 8:684.
Vosberg et al. (1977) Biochemistry 16:3633.
Wong et al. (1991) Biochemistry 30:526.
Fu et al. (1997) Nucleic Acids Research 25:677.
Jones (1997) BioTechniques 22:938.
LeBel et al. (1980) J. Biol. Chem. 256:1227.
Zimmerman (1990) Nucleic Acids Research 18:1067.
Ronaghi et al., "A Sequencing Method Based on Real–Time Pryophospate", *Science*, vol. 281, Jul. 17, 1998, pp. 363 and 365.

\* cited by examiner

SEQUENCE LISTING

<160> NUMBER OF SEQ ID NOS: 6

<210> SEQ ID NO 1
<211> LENGTH: 55
<212> TYPE: DNA
<213> ORGANISM: Artificial Sequence
<220> FEATURE:
<223> OTHER INFORMATION: Oligonucleotides primer

<400> SEQUENCE: 1
cgacgatctg aggtcatagc tgtttcctgt gtgaactggc cgtcgtttta caacg     55

<210> SEQ ID NO 2
<211> LENGTH: 35
<212> TYPE: DNA
<213> ORGANISM: Artificial Sequence
<220> FEATURE:
<223> OTHER INFORMATION: Oligonucleotides primer

<400> SEQUENCE: 2
gctggaattc gtcagactgg ccgtcgtttt acaac     35

<210> SEQ ID NO 3
<211> LENGTH: 17
<212> TYPE: DNA

```
<213> ORGANISM: Artificial Sequence
<220> FEATURE:
<223> OTHER INFORMATION: Oligonucleotides primer

<400> SEQUENCE: 3
ctaaaacgac ggccagt                                                      17

<210> SEQ ID NO 4
<211> LENGTH: 51
<212> TYPE: DNA
<213> ORGANISM: Artificial Sequence
<220> FEATURE:
<223> OTHER INFORMATION: Oligonucleotides primer

<400> SEQUENCE: 4
agcttgggtt cgaggagatc ttccgggtta cggcggaaga tctcctcgag g                51

<210> SEQ ID NO 5
<211> LENGTH: 51
<212> TYPE: DNA
<213> ORGANISM: Artificial Sequence
<220> FEATURE:
<223> OTHER INFORMATION: Oligonucleotides primer

<400> SEQUENCE: 5
agctcctcga ggagatcttc cgccgtaacc cggaagatct cctcgaaccc a                51

<210> SEQ ID NO 6
<211> LENGTH: 25
<212> TYPE: DNA
<213> ORGANISM: Artificial Sequence
<220> FEATURE:
<223> OTHER INFORMATION: Oligonucleotides primer

<400> SEQUENCE: 6
cgaggagatc ttccgggtta cggcg                                             25
```

METHOD OF SEQUENCING DNA

This invention relates to a method of sequencing DNA, based on the detection of base incorporation by the release of pyrophosphate (PPi). In particular, the invention relates to a "real-time" sequencing method.

DNA sequencing is an essential tool in molecular genetic analysis. The ability to determine DNA nucleotide sequences has become increasingly important as efforts have commenced to determine the sequences of the large genomes of humans and other higher organisms. The two most commonly used methods for DNA sequencing are the enzymatic chain-termination method of Sanger and the chemical cleavage technique of Maxam and Gilbert. Both methods rely on gel electrophoresis to resolve, according to their size, DNA fragments produced from a larger DNA segment. Since the electrophoresis step as well as the subsequent detection of the separated DNA-fragments are cumbersome procedures, a great effort has been made to automate these steps. However, despite the fact that automated electrophoresis units are commercially available, electrophoresis is not well suited for large-scale genome projects or clinical sequencing where relatively cost-effective units with high throughput are needed. Thus, the need for non-electrophoretic methods for sequencing is great and several alternative strategies have been described, such as scanning tunnel electron microscopy (Driscoll et al., 1990, Nature, 346, 294–296), sequencing by hybridization (Bains et al., 1988, J. Theo. Biol. 135, 308–307) and single molecule detection (Jeff et al., 1989, Biomol. Struct. Dynamics, 7, 301–306), to overcome the disadvantages of electrophoresis.

Techniques enabling the rapid detection of a single DNA base change are also important tools for genetic analysis. In many cases detection of a single base or a few bases would be a great help in genetic analysis since several genetic diseases and certain cancers are related to minor mutations. A mini-sequencing protocol based on a solid phase principle was described (Hultman, et al., 1988, Nucl. Acid. Res., 17, 4937–4946; Syvanen et al., 1990, Genomics, 8, 684–692). The incorporation of a radiolabeled nucleotide was measured and used for analysis of the three-allelic polymorphism of the human apolipoprotein E gene. However, radioactive methods are not well suited for routine clinical applications and hence the development of a simple non-radioactive method for rapid DNA sequence analysis has also been of interest.

Methods of sequencing based on the concept of detecting inorganic pyrophosphate (PPi) which is released during a polymerase reaction have been described (WO 93/23564 and WO 89/09283). As each nucleotide is added to a growing nucleic acid strand during a polymerase reaction, a pyrophosphate molecule is released. It has been found that pyrophosphate released under these conditions can be detected enzymically e.g. by the generation of light in the luciferase-luciferin reaction. Such methods enable a base to be identified in a target position and DNA to be sequenced simply and rapidly whilst avoiding the need for electrophoresis and the use of harmful radiolabels.

However, the PPi-based sequencing methods mentioned above are not without drawbacks. Firstly, it has been found that dATP used in the sequencing reaction (chain extension) interferes in the subsequent luciferase-based detection reaction, by acting as a substrate for the luciferase enzyme. In many circumstances, this interference severely limits the utility of the method.

Secondly whilst the PPi-based methods described above do represent an improvement in ease and speed of operation, there is still a need for improved methods of sequencing which allow rapid detection and provision of sequence information. In particular there is a need for "real-time" methods of sequencing which enable the sequence information to be revealed simultaneously with, or very shortly after the sequencing, chain extension, reaction.

We now propose a novel modified PPi-based sequencing method in which these problems are addressed and which permits the sequencing reactions to be continuously monitored in real-time, with a signal being generated and detected, as each nucleotide is incorporated. This is achieved by using an dATP analogue, in place of dATP, which does not interfere with the luciferase reaction, and by performing the chain extension and detection, or signal-generation, reactions substantially simultaneously by including the "detection enzymes" in the chain extension reaction mixture. This represents a departure from the approach reported in the PPi-based sequencing proposed above, in which the chain extension reaction is first performed separately as a first reaction step, followed by a separate "detection" reaction, in which the products of the extension reaction are subsequently subjected to the luciferin-luciferase based signal generation ("detection") reactions.

In one aspect, the present invention thus provides a method of identifying a base at a target position in a single-stranded sample DNA sequence wherein an extension primer, which hybridises to the sample DNA immediately adjacent to the target position is provided and the sample DNA and extension primer are subjected to a polymerase reaction in the presence of a deoxynucleotide or dideoxynucleotide whereby the deoxynucleotide or dideoxynucleotide will only become incorporated and release pyrophosphate (PPi) if it is complementary to the base in the target position, any release of PPi being detected enzymically, different deoxynucleotides or dideoxynucleotides being added either to separate aliquots of sample-primer mixture or successively to the same sample-primer mixture and subjected to the polymerase reaction to indicate which deoxynucleotide or dideoxynucleotide is incorporated, characterised in that, the PPi-detection enzyme(s) are included in the polymerase reaction step and in that in place of deoxy- or dideoxy adenosine triphosphate (ATP) a dATP or ddATP analogue is used which is capable of acting as a substrate for a polymerase but incapable of acting as a substrate for a said PPi-detection enzyme.

The term dideoxynucleotide as used herein includes all 2'-deoxynucleotides in which the 3'-hydroxyl group is absent or modified and thus, while able to be added to the primer in the presence of the polymerase, is unable to enter into a subsequent polymerisation reaction.

PPi can be determined by many different methods and a number of enzymatic methods have been described in the literature (Reeves et al., (1969), Anal. Biochem., 28, 282–287; Guillory et al., (1971), Anal. Biochem., 39, 170–180; Johnson et al., (1968), Anal. Biochem., 15, 273; Cook et al., (1978), Anal. Biochem. 91, 557–565; and Drake et al., (1979), Anal. Biochem. 94, 117–120).

It is preferred to use luciferase and luciferin in combination to identify the release of pyrophosphate since the amount of light generated is substantially proportional to the amount of pyrophosphate released which, in turn, is directly proportional to the amount of base incorporated. The amount of light can readily be estimated by a suitable light sensitive device such as a luminometer.

Luciferin-luciferase reactions to detect the release of PPi are well known in the art. In particular, a method for continuous monitoring of PPi release based on the enzymes ATP sulphurylase and luciferase has been developed by Nyren and Lundin (Anal. Biochem., 151, 504–509, 1985) and termed ELIDA (Enzymatic Luminometric Inorganic Pyrophosphate Detection Assay). The use of the ELIDA method to detect PPi is preferred according to the present invention. The method may however be modified, for example by the use of a more thermostable luciferase (Kaliyama et al., 1994, Biosci. Biotech. Biochem., 58, 1170–1171). This method is based on the following reactions:

ATP sulphurylase

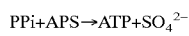

luciferase

(APS=adenosine 5'-phosphosulphate)

The preferred detection enzymes involved in the PPi detection reaction are thus ATP sulphurylase and luciferase.

To carry out the method of the invention, the detection enzymes are included in the polymerase reaction step ie. in the chain extension reaction step. Thus the detection enzymes are added to the reaction mix for the polymerase step prior to, simultaneously with or during the polymerase reaction. In the case of an ELIDA detection reaction, the reaction mix for the polymerase reaction may thus include at least one nucleotide (deoxy- or dideoxy), polymerase, luciferin, APS, ATP suphurylase and luciferase. The polymerase reaction may be initiated by addition of the polymerase or, more preferably the nucleotide, and preferably the detection enzymes are already present at the time the reaction is initiated, or they may be added with the reagent that initiates the reaction.

The present invention thus permits PPi release to be detected during the polymerase reaction giving a real-time signal. The sequencing reactions may be continuously monitored in real-time. A procedure for rapid detection of PPi release is thus enabled by the present invention. The ELIDA rections have been estimated to take place in less than 2 seconds (Nyren and Lundin, supra). The rate limiting step is the conversion of PPi to ATP by ATP sulphurylase, while the luciferase reaction is fast and has been estimated to take less than 0.2 seconds. Incorporation rates for polymerases have also been estimated by various methods and it has been found, for example, that in the case of Klenow polymerase, complete incorporation of one base may take less than 0.5 seconds. Thus, the estimated total time for incorporation of one base and detection by ELIDA is approximately 3 seconds. It will be seen therefore that very fast reaction times are possible, enabling real-time detection. The reaction times could further be decreased by using a more thermostable luciferase.

A further feature of the invention is the use of a dATP or ddATP analogue which does not interfere in the enzymatic PPi detection reaction but which nonetheless may be normally incorporated into a growing DNA chain by a polymerase. By "normally incorporated" is meant that the nucleotide is incorporated with normal, proper base pairing. In the preferred enbodiment of the invention where luciferase is the PPi detection enzyme, the preferred analogues for use according to the invention are the [1-thio]triphosphate (or α-thiotriphosphate) analogues of deoxy or dideoxy ATP, preferably deoxyadenosine [1-thio]triphospate, or deoxyadenosine α-thiotriphosphate (dATPαS) as it is also known. dATPαS, along with the α-thio analogues of dCTP, dGTP and dTTP, may be purchased from New England Nuclear Labs. As will be described in the Example below, experiments have shown that substituting dATP with dATPαS allows efficient incorporation by the polymerase with a low background signal due to the absence of an interaction between dATPαS and luciferase. The signal to noise ratio is increased according to the present invention by using a nucleotide analogue in place of dATP, which eliminates the background caused by the ability of dATP to function as a substrate for luciferase. In particular, we have found that an efficient incorporation with the polymerase is achieved while the background signal due to the generation of light by the luciferin-luciferase system resulting from dATP interference is substantially decreased.

Where ATP is present in the reaction mixture during or after chain extension, for example as an impurity or as a contaminant of dATP added as the source of the base to be incorporated, it will also interfere in the pyrophosphate luciferin system and give an incorrect luminescence reading. It may be advantageous, therefore, to remove ATP from reagent solutions prior to addition to the reaction mix. This can be achieved by contacting the solution with an immobilised enzyme which converts ATP into a product which is no longer a substrate for luciferase. Such enzymes include, in particular, apyrase which converts the ATP to AMP and two molecules of phosphate. The immobilised enzyme may then be removed prior to the chain extension/detection. It is particularly convenient to use magnetic beads such as Dynabeads® (sold by Dynal AS, Oslo, Norway) as the solid support due to the ease with which such beads can be removed from contact with the solution using a magnet. Generally, however such ATP removal steps have not been found to be necessary according to the present invention.

In order to repeat the method cyclically and thereby sequence the sample DNA and, also to aid separation of the single stranded sample DNA from its complementary strand, it is desirable that the sample DNA is immobilised or provided with means for attachment to a solid support. Moreover, the amount of sample DNA available may be small and it may therefore be desirable to amplify the sample DNA before carrying out the method according to the invention.

The sample DNA may be amplified, for example in vitro by PCR or Self Sustained Sequence Replication (3SR) or in vivo using a vector and, if desired, in vitro and in vivo amplification may be used in combination. Whichever method of amplification is used it is desirable that the amplified DNA becomes immobilised or is provided with means for attachment to a solid support. For example, a PCR primer may be immobilised or be provided with means for attachment to a solid support. Also, a vector may comprise means for attachment to a solid support adjacent the site of insertion of the sample DNA such that the amplified sample DNA and the means for attachment may be excised together.

Immobilisation of the amplified DNA may take place as part of PCR amplification itself, as where one or more primers are attached to a support, or alternatively one or more of the PCR primers may carry a functional group permitting subsequent immobilisation, eg. a biotin or thiol group. Immobilisation by the 5' end of a primer allows the strand of DNA emanating from that primer to be attached to a solid support and have its 3' end remote from the support and available for subsequent hybridisation with the extension primer and chain extension by polymerase.

The solid support may conveniently take the form of microtitre wells, which are advantageously in the conventional 8x12 format, or dipsticks which may be made of polystyrene activated to bind the primer DNA (K Almer, Doctoral Theses, Royal Institute of Technology, Stockholm, Sweden, 1988). However, any solid support may conveniently be used including any of the vast number described in the art, eg. for separation/immobilisation reactions or solid phase assays. Thus, the support may also comprise particles, fibres or capillaries made, for example, of agarose, cellulose, alginate, Teflon or polystyrene. Magnetic particles eg the superparamagnetic beads produced by Dynal AS (Oslo, Norway) are a preferred support since they can be readily isolated from a reaction mixture yet have superior reaction kinetics over many other forms of support.

The solid support may carry functional groups such as hydroxyl, carboxyl, aldehyde or amino groups, or other moieties such as avidin or streptavidin, for the attachment of primers. These may in general be provided by treating the support to provide a surface coating of a polymer carrying one of such functional groups, e.g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. U.S. Pat. No. 4,654,267 describes the introduction of many such surface coatings.

The assay technique is very simple and rapid, thus making it easy to automate by using a robot apparatus where a large number of samples may be rapidly analysed. Since the preferred detection and quantification is based on a luminometric reaction this can be easily followed spectrophotometrically. The use of luminometers is well known in the art and described in the literature.

The real-time pyrophosphate detection method of the present invention thus opens up the possibility for an automated approach for large-scale, non-elecrophoretic solid-phase sequencing procedures, which allow for continuous measurement of the progress of the polymerisation reaction with time. The method of the invention also has the advantage that multiple samples may be handled in parallel.

The target DNA may be cDNA synthesised from RNA in the sample and the method of the invention is thus applicable to diagnosis on the basis of characteristic RNA. Such preliminary synthesis can be carried out by a preliminary treatment with a reverse transcriptase, conveniently in the same system of buffers and bases of subsequent PCR steps if used. Since the PCR procedure requires heating to effect strand separation, the reverse transcriptase will be inactivated in the first PCR cycle. When mRNA is the sample nucleic acid, it may be advantageous to submit the initial sample, e.g. a serum sample, to treatment with an immobilised polydT oligonucleotide in order to retrieve all mRNA via the terminal polyA sequences thereof. Alternatively, a specific oligonucleotide sequence may be used to retrieve the RNA via a specific RNA sequence. The oligonucleotide can then serve as a primer for cDNA synthesis, as described in WO 89/0982.

Advantageously, the extension primer is sufficiently large to provide appropriate hybridisation with the sequence immediately 5' of the target position, yet still reasonably short in order to avoid unnecessary chemical synthesis. It will be clear to persons skilled in the art that the size of the extension primer and the stability of hybridisation will be dependent to some degree on the ratio of A–T to C–G base pairings, since more hydrogen bonding is available in a C–G pairing. Also, the skilled person will consider the degree of homology between the extension primer to other parts of the amplified sequence and choose the degree of stringency accordingly. Guidance for such routine experimentation can be found in the literature, for example, Molecular Cloning: a laboratory manual by Sambrook, J., Fritsch E. F. and Maniatis, T. (1989). If four aliquots are used, the extension primer is preferably added before the sample is divided into four aliquots although it may be added separately to each aliquot. It should be noted that the extension primer may be identical with the PCR primer but preferably it is different, to introduce a further element of specificity into the system.

Alternatively, a primer with a phosphorylated 5'-end, containing a loop and annealing back on itself and the 3'-end of the single stranded template can be used. If the 3'-end of the template has the sequence region denoted T (template), the primer has the following sequence starting from the 5'-end; P-L-P'-T', where P is primer specific (5 to 30 nucleotides), L is loop (preferably 4 to 10 nucleotides), P' is complementary to P (preferably 5 and 30 nucleotides) and T' is complementary to the template sequence in the 3'-end (T) (at least 4 nucleotides). This primer can then be ligated to the single stranded template using t4 DNA ligase or a similar enzyme. This provides a covalent link between the template and the primer, thus avoiding the possibility that the hybridised primer is washed away during the protocol.

The polymerase reaction in each aliquot in the presence of the extension primer and a deoxynucleotide is carried out using a polymerase which will incorporate dideoxynucleotides, e.g. T7 polymerase, Klenow or Sequenase Ver. 2.0 (USB U.S.A.). However, it is known that many polymerases have a proof-reading or error checking ability and that 3' ends available for chain extension are sometimes digested by one or more nucleotides. If such digestion occurs in the method according to the invention the level of background noise increases. In order to avoid this problem, a nonproof-reading polymerase, eg. exonuclease deficient (exo$^-$) Klenow polymerase may be used. Otherwise it is desirable to add to each aliquot fluoride ions or nucleotide monophosphates which suppress 3' digestion by polymerase.

In the method of the invention it is preferred to use a DNA polymerase with high efficiency in each extension step due to the rapid increase of background signal which may take place if templates which are not fully extended accumulate. A high fidelity in each step is also desired, which can be achieved by using polymerases with exonuclease activity. However, this has the disadvantage mentioned above that primer degradation can be obtained. Although the exonuclease activity of the Klenow polymerase is low, we have found that the 3' end of the primer was degraded with longer incubations in the absence of nucleotides. An induced-fit binding mechanism in the polymerisation step selects very efficiently for binding of the correct dNTP with a net contribution towards fidelity of $10^5$–$10^6$. Exonuclease-deficient polymerases, such as (exo$^-$) Klenow or Sequenase 2.0, catalysed incorporation of a nucleotide which was only observed when the complementary dNTP was present, confirming a high fidelity of these enzymes even in the absence of proof-reading exonuclease activity. The main advantage of using (exo$^-$) Klenow DNA polymerase over Sequenase 2.0 is its lower Km for nucleotides, allowing a high rate of nucleotide incorporation even at low nucleotide concentrations. It is also possible to replace all dNTPs with nucleotide analogues or non-natural nucleotides such as dNTPαS, and such analogues may be preferable for use with a DNA polymerase having exonuclease activity.

In many diagnostic applications, for example genetic testing for carriers of inherited disease, the sample will contain heterozygous material, that is half the DNA will have one nucleotide at the target position and the other half will have another nucleotide. Thus if four aliquots are used in a preferred method according to the invention, two will show a negative signal and two will show half the positive signal. It will be seen therefore that it is desirable quantitatively to determine the amount of signal detected in each sample. Also, it will be appreciated that if two or more of the same base are adjacent the 3'-end of the primer a larger signal will be produced. In the case of a homozygous sample it will be clear that there will be three negative and one positive signal when the same is in four aliquots.

It will be appreciated that when the target base immediately 3'- of the primer has an identical base 3'-thereto, and the polymerisation is effected with a deoxynucleotide (rather than a dideoxynucleotide) the extension reaction will add two bases at the same time and indeed any sequence of successive identical bases in the sample will lead to simultaneous incorporation of corresponding bases into the primer. However, the amount of pyrophosphate liberated will clearly be proportional to the number of incorporated bases so that there is no difficulty in detecting such repetitions.

Since the primer is extended by a single base by the procedure described above (or a sequence of identical bases), the extended primer can serve in exactly the same way in a repeated procedure to determine the next base in the sequence, thus permitting the whole sample to be sequenced. Immobilisation of the sample and hybridised primer permits washing to separate unwanted deoxynucleotides before proceeding to the next step.

The present invention provides two principal methods of sequencing immobilised DNA.

A. The invention provides a first method of sequencing sample DNA wherein the sample DNA is subjected to amplification; the amplified DNA is immobilised and then subjected to strand separation, the non-immobilised strand being removed and an extension primer is provided, which primer hybridises to the immobilised DNA immediately adjacent that portion of the DNA to be sequenced; each of four aliquots of the immobilised single stranded DNA is then subjected to a polymerase reaction in the presence of a deoxynucleotide, each aliquot using a different deoxynucleotide whereby only the deoxynucleotide complementary to the base in the target position becomes incorporated; pyrophosphate released by base incorporation being identified; the immobilised sample and primer then being separated from the reaction solution and the incorporated base added to the unreacted aliquots of sample/primer under polymerising conditions to extend the primer in all the aliquots by the said incorporated base and the immobilised sample/primer then being separated from the reaction solution, the process being repeated to sequence the sample DNA.

B. The invention also provides a second method of sequencing sample DNA wherein the sample DNA is subjected to amplification; the amplified DNA is immobilised and then subjected to strand separation, the non-immobilised strand being removed and an extension primer is provided, which primer hybridises to the immobilised DNA immediately adjacent that portion of the DNA to be sequenced; immobilised single stranded DNA is then subjected to a polymerase reaction in the presence of a first deoxynucleotide, and the extent of pyrophosphate release is determined, where necessary the immobilised sample and primer being separated from the reaction mixture and the reaction being repeated by successive addition of a second, third and fourth deoxynucleotide until a positive release of pyrophosphate indicates incorporation of a particular deoxynucleotide into the primer, whereupon the procedure is repeated to extend the primer one base at a time and to determine the base which is immediately 3'- of the extended primer at each stage.

An alternative format for the analysis is to use an array format wherein samples are distributed over a surface, for example a microfabricated chip, and thereby an ordered set of samples may be immobilized in a 2-dimensional format. Many samples can thereby be analysed in parallel. Using the method of the invention, many immobilized templates may be analysed in this was by allowing the solution containing the enzymes and one nucleotide to flow over the surface and then detecting the signal produced for each sample. This procedure can then be repeated. Alternatively, several different oligonucleotides complementary to the template may be distributed over the surface followed by hybridization of the template. Incorporation of deoxynucleotides or dideoxynucleotides may be monitored for each oligonucleotide by the signal produced using the various oligonucleotides as primer. By combining the signals from different areas of the surface, sequence-based analyses may be performed by four cycles of polymerase reactions using the various dideoxynucleotides.

Two-stage PCR (using nested primers), as described in our co-pending application WO90/11369, may be used to enhance the signal to noise ratio and thereby increase the sensitivity of the method according to the invention. By such preliminary amplification, the concentration of target DNA is greatly increased with respect to other DNA which may be present in the sample and a second-stage amplification with at least one primer specific to a different sequence of the target DNA significantly enhances the signal due to the target DNA relative to the 'background noise'.

Regardless of whether one-stage or two stage PCR is performed, the efficiency of the PCR is not critical since the invention relies on the distinct difference different from the aliquots. However, as mentioned above, it is preferred to run an initial qualitative DIANA as a check for the presence or absence of amplified DNA.

Any suitable polymerase may be used, although it is preferred to use a thermophilic enzyme such as Taq polymerase to permit the repeated temperature cycling without having to add further polymerase, e.g. Klenow fragment, in each cycle of PCR.

PCR has been discussed above as a preferred method of initially amplifying target DNA although the skilled person will appreciate that other methods may be used instead of in combination with PCR. A recent development in amplification techniques which does not require temperature cycling or use of a thermostable polymerase is Self Sustained Sequence Replication (3SR). 3SR is modelled on retroviral replication and may be used for amplification (see for example Gingeras, T. R. et al PNAS (USA) 87:1874–1878 and Gingeras, T. R. et al PCR Methods and Applications Vol. 1, pp 25–33).

As indicated above, the method can be applied to identifying the release of pyrophosphate when dideoxynucleotide residues are incorporated into the end of a DNA chain. WO93/23562 relates to a method of identification of the base in a single target position in a DNA sequence (minisequencing) wherein sample DNA is subjected to amplification; the amplified DNA is immobilised and then subjected to strand separation, the non-immobilised strand being removed and an extension primer, which hybridises to the immobilised DNA immediately adjacent to the target position, is provided; each of four aliquots of the immobilised single stranded DNA is then subjected to a polymerase reaction in the presence of a dideoxynucleotide, each aliquot using a different dideoxynucleotide whereby only the dideoxynucleotide complementary to the base in the target position becomes incorporated; the four aliquots are then subjected to extension in the presence of all four deoxynucleotides, whereby in each aliquot the DNA which has not reacted with the dideoxynucleotide is extended to form double stranded DNA while the dideoxy-blocked DNA remains as single stranded DNA; followed by identification of the double stranded and/or single stranded DNA to indicate which dideoxynucleotide was incorporated and hence which base was present in the target position. Clearly, the release of pyrophosphate in the chain terminating dideoxynucleotide reaction will indicate which base was incorporated but the relatively large amount of pyrophosphate released in the subsequent deoxynucleotide primer extension reactions (so-called chase reactions) gives a much larger signal and is thus more sensitive.

It will usually be desirable to run a control with no dideoxynucleotides and a 'zero control' containing a mixture of all four dideoxynucleotides.

WO93/23562 defines the term 'dideoxynucleotide' as including 3'-protected 2'-deoxynucleotides which act in the same way by preventing further chain extension. However, if the 3' protecting group is removable, for example by hydrolysis, then chain extension (by a single base) may be followed by unblocking at the 3' position, leaving the extended chain ready for a further extension reaction. In this way, chain extension can proceed one position at a time without the complication which arises with a sequence of identical bases, as discussed above. Thus, the methods A and B referred to above can be modified whereby the base added at each stage is a 3'-protected 2'-deoxynucleotide and after the base has been added (and the light emission detected), the 3'-blocking group is removed to permit a further 3'-protected—2'-deoxynucleotide to be added. Suitable protecting groups include acyl groups such as alkanol grouops e.g. acetyl or indeed any hydroxyl protecting groups known in the art, for example as described in Protective Groups in Organic Chemistry, J F W McOnie, Plenum Press, 1973.

The invention, in the above embodiment, provides a simple and rapid method for detection of single base changes. In a preferred format it successfully combines two techniques: solid-phase technology (DNA bound to magnetic beads) and an Enzymic Luminometric Detection Assay (ELIDA). The method can be used to both identify and quantitate selectively amplified DNA fragments. It can also be used for detection of single base substitutions and for estimation of the heterozygosity index for an amplified polymorphic gene fragment. This means that the method can be used to screen for rare point mutations responsible for both acquired and inherited diseases, identify DNA polymorphisms, and even differentiate between drug-resistant and drug-sensitive strains of viruses or bacteria without the need for centrifugations, filtrations, extractions or electrophoresis. The simplicity of the method renders it suitable for many medical (routine analysis in a wide range of inherited disorders) and commercial applications.

The positive experimental results presented below clearly show the method is applicable to an on-line automatic non-electrophoretic solid phase DNA sequencing approach, with step-wise incorporation of single deoxynucleotides. After amplification, immobilization on magnetic beads, melting to yield single-stranded DNA and annealing of the primer, the template/primer-fragment is used in a repeated cycle of dNTP incubation and washing. Samples are continuously monitored in the ELIDA. As the synthesis of DNA is accompanied by release of inorganic pyrophosphate (PPi) in an amount equal to the amount of nucleotide incorporated, signals in the ELIDA are observed only when complementary bases are incorporated. Due to the ability of the method to determine PPi quantitatively, it is possible to distinguish incorporation of a single base from two or several simultaneous incorporations. Since the DNA template is preferably obtained by PCR, it is relatively straight forward to increase the amount of DNA needed for such an assay.

As mentioned above our results open the possibility for a novel approach for large-scale non-electrophoretic solid phase DNA sequencing, which allows for continuous determination of the progress of the polymerisation reaction with time. For the success of such an approach there is a need for high efficiency of the DNA polymerase due to the rapid increase of background signal if templates accumulate which are not "in phase". The new approach has several advantages as compared to standard sequencing methods. Firstly, the method is suitable for handling of multiple samples in parallel. Secondly, relatively cost-effective instruments can be envisioned. In addition, the method avoids the use of electrophoresis and thereby the loading of samples and casting of gels.

Advantageously, the method according to the present invention may be combined with the method taught in WO93/23563 which uses PCR to introduce loop structures which provide a permanently attached 3' primer at the 3' terminal of a DNA strand of interest. For example, in such a modified method, the extension primer is introduced as part of the 3'-terminal loop structure onto a target sequence of one strand of double stranded DNA which contains the target position, said target sequence having a region A at the 3'-terminus thereof and there being optionally a DNA region B which extends 3' from region A, whereby said double-stranded DNA is subjected to polymerase chain reaction (PCR) amplification using a first primer hybridising to the 3'-terminus of the sequence complementary to the target sequence, which first primer is immobilised or provided with means for attachment to a solid support, and a second primer having a 3'-terminal sequence which hybridises to at least a portion of A and/or B of the target sequence while having at its 5'-end a sequence substantially identical to A, said amplification producing double-stranded target DNA having at the 3'-end of the target sequence, in the following order, the region A, a region capable of forming a loop and a sequence A' complementary to sequence A, whereafter the amplified double-stranded DNA is subjected in immobilised form to strand separation whereby the non-immobilised target strand is liberated and region A' is permitted or caused to hybridise to region A, thereby forming said loop. The 3' end of region A' hybridises immediately adjacent the target position. The dideoxy and/or extension reactions use the hybridised portion as a primer. Experiments using this principle have been performed successfully, as illustrated in the Examples herein.

The invention also comprises kits for use in methods of the invention which will normally include at least the following components:
   (a) a test specific primer which hybridises to sample DNA so that the target position is directly adjacent to the 3' end of the primer;
   (b) a polymerase;
   (c) detection enzyme means for identifying pyrophosphate release;
   (d) deoxynucleotides including, in place of dATP, a dATP analogue which is capable of acting as a substrate for a polymerase but incapable of acting as a substrate for a said PPi-detection enzyme; and (e) optionally dideoxynucleotides, optionally ddATP being replaced by a ddATP analogue which is capable of acting as a substrate for a polymerase but incapable of acting as a substrate for a said PPi-detection enzyme.

If the kit is for use with initial PCR amplification then it will also normally include at least the following components:

(i) a pair of primers for PCR, at least one primer having means permitting immobilisation of said primer;

(ii) a polymerase which is preferably heat stable, for example Taq1 polymerase;

(iii) buffers for the PCR reaction; and (iv) deoxynucleotides.

Where an enzyme label is used to evaluate PCR, the kit will advantageously contain a substrate for the enzyme and other components of a detection system.

Figure 2:
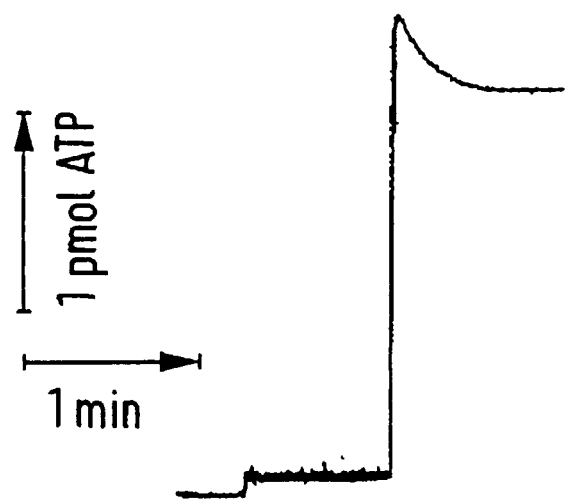
Figure 3:
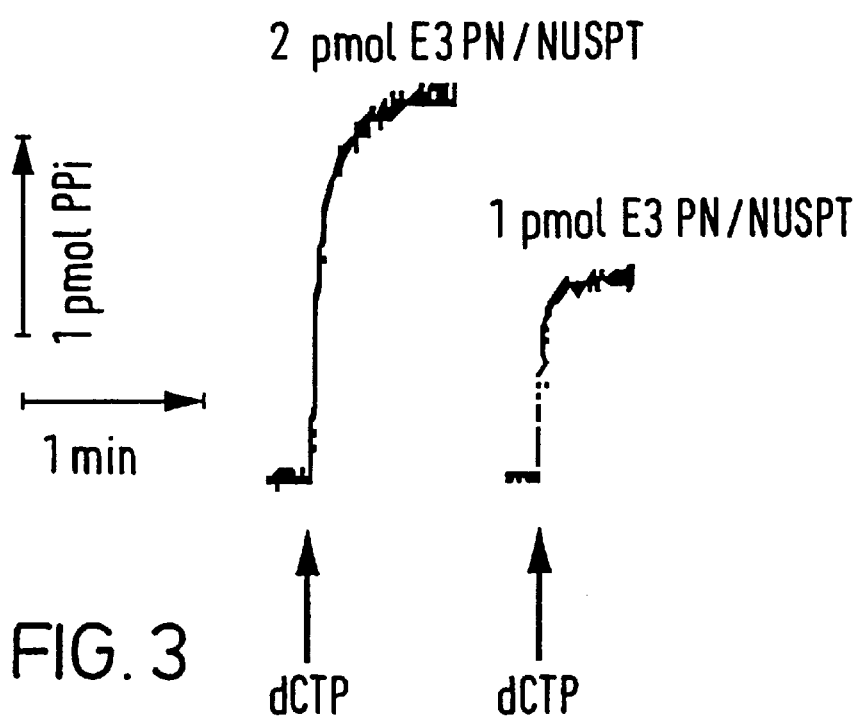
Figure 4:
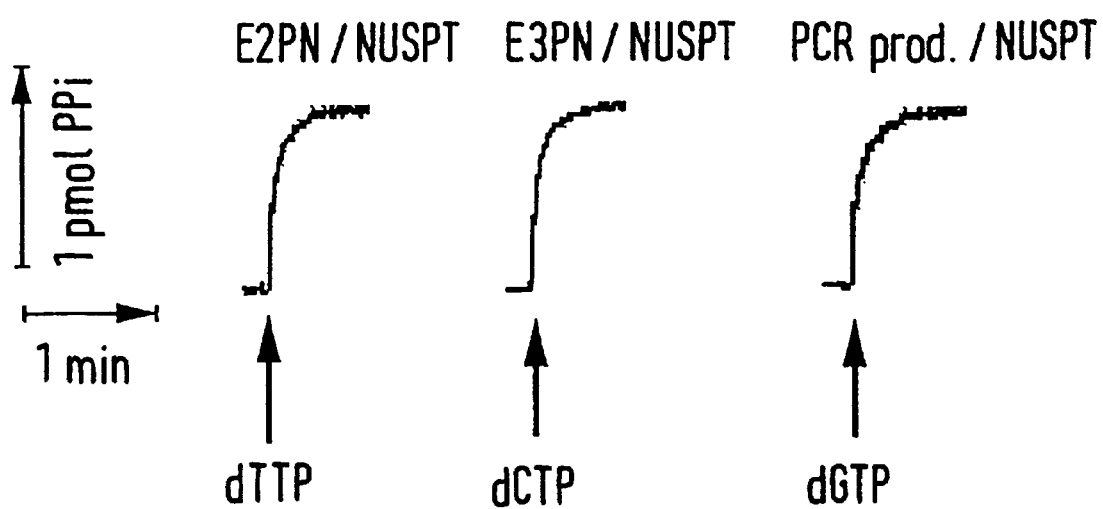
Figure 5:
Figure 6:
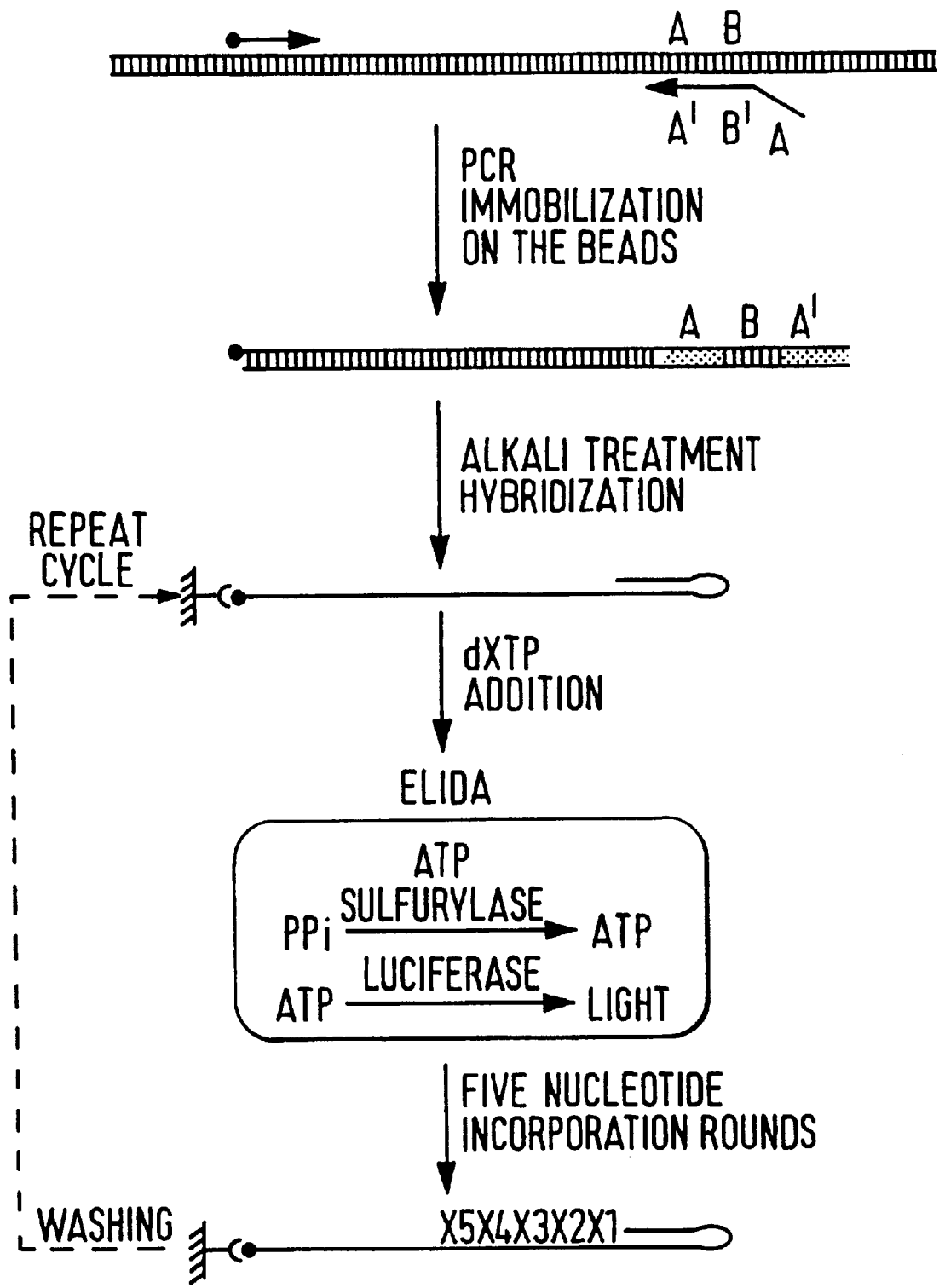
Figure 7:
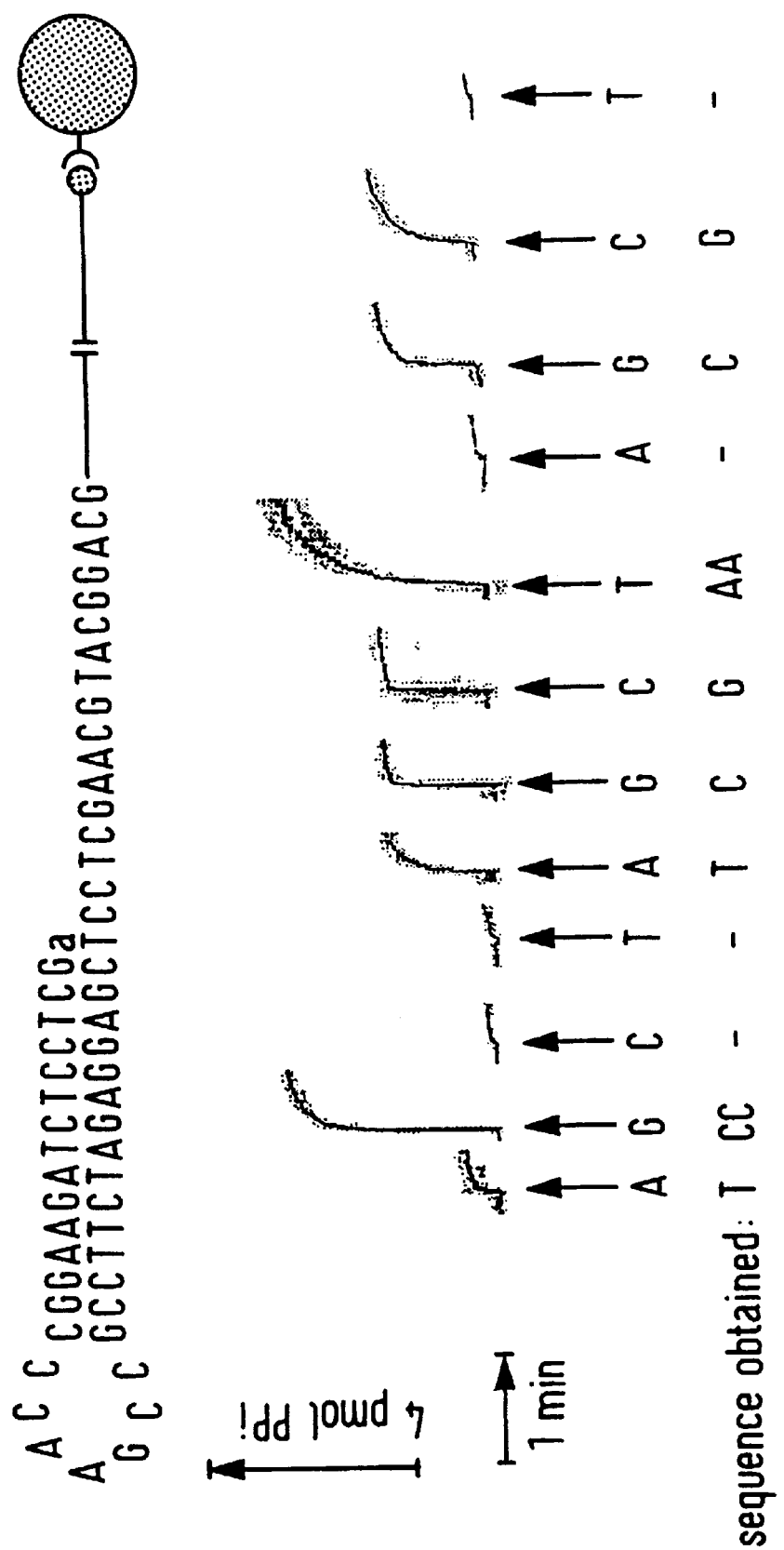
Figure 8:
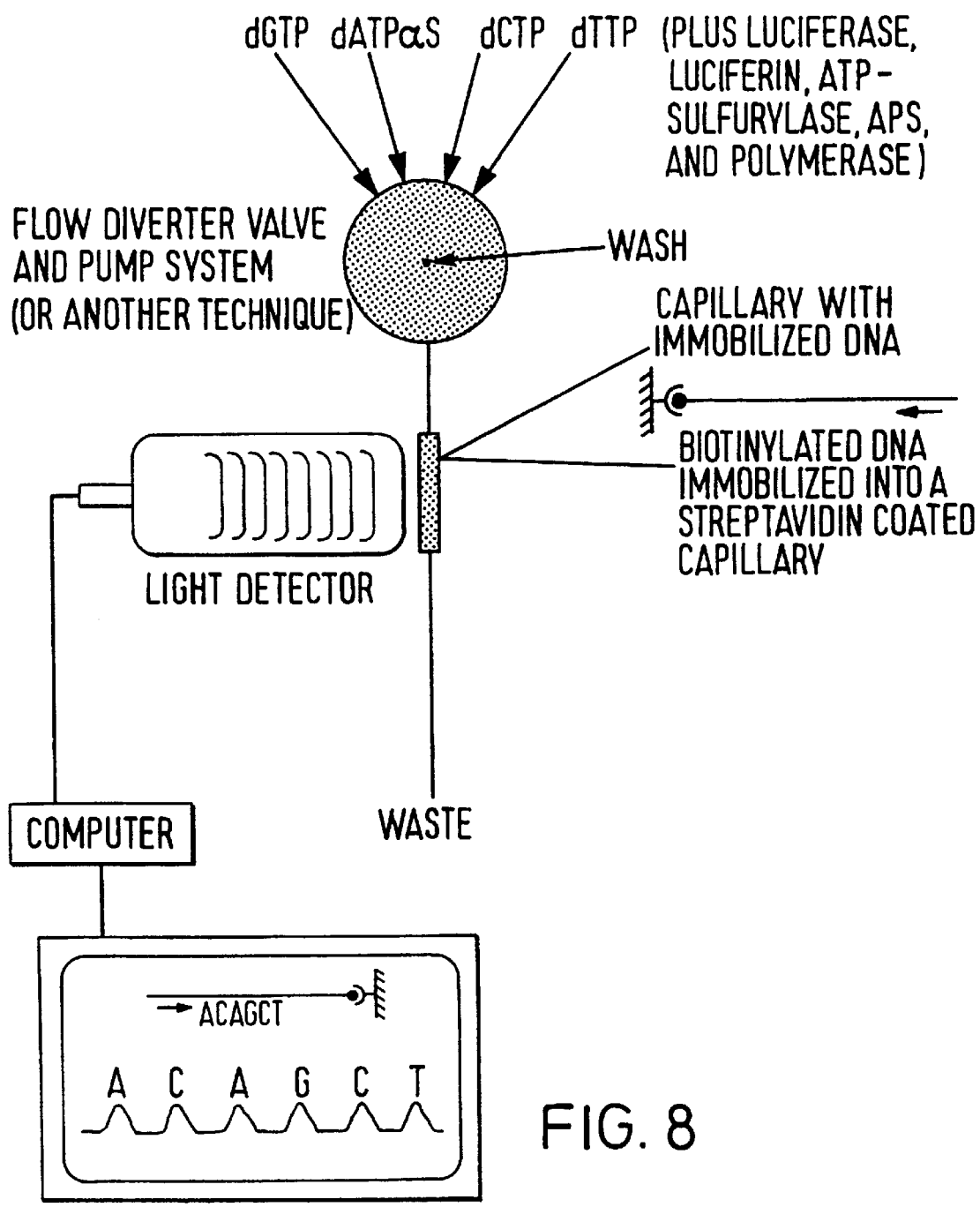

The invention will now be described by way of a non-limiting Example with reference to the drawings in which:

FIG. 1 is a schematic representation of the real-time DNA sequencing method. The four different nucleotides are added stepwise to the immobilised template hybridised to a primer. The PPi released in the DNA polymerase catalysed reaction, is detected by the ATP sulfurylase and luciferase catalysed reactions. The height of the signal is proportional to the number of bases which have been incorporated. After each base addition a washing step is performed. These steps are repeated in a cycle and the sequence of the template is deduced;

FIG. 2 shows the effect of dATP and dATPαS on the luciferase reaction. 0.1 nmol dATP and 8 nmol dATPαS were added as indicatsd and the luminescence output was detected;

FIG. 3 shows the extent of PPi synthesis as a function of template concentration. Three pmol (exo⁻) Klenow were incubated with 1 or 2 pmol E3PN/NUSPT as indicated. The reactions were started by the addition of 40 pmol dCTP. The PPi released were detected by the ELIDA;

FIG. 4 shows real-time detection of one base incorporation on three different tempiates 1.5 pmol indicated templates were incubated with 3 pmol of (exo⁻) Klenow. The reactions were started by addition of 40 pmol of the indicated deoxynucleotide and the PPi released were detected by the ELIDA;

FIG. 5 shows real-time DNA sequencing performed on 291-base-long PCR-generated single-stranded template immobilised on streptavidin coated paramagnetic beads. About 1 pmol of the template/primer (NUSPT) was incubated with 3 pmol (exo⁻) Klenow. The reaction was started by the addition of 40 pmol of the indicated deoxynucleotide and the PPi released were detected by the ELIDA. Between each nucleotide addition the beads were washed. The given ELIDA signals are compensated for the loss of beads during the washing procedures. The DNA-sequence after the primer, as confirmed by semi-automated solid-phase DNA-sequencing, is inserted in the figure;

FIG. 6 shows a schematic representation of using PCR to generate a loop-structure with one of the primers biotinylated. The PCR-product is immobilised and the non-biotinylated strand is eluted with alkali. The biotinylated strand is allowed to hybridise to form a loop-structure. The loop-structure was used as a template for real-time DNA sequencing as illustrated in FIG. 1 and described in Example 1;

FIG. 7 shows real-time DNA sequencing performed on a PCR-generated loop-structure immobilised on streptavidin-coated paramagnetic beads. About 2 pmol of the template was incubated with 3 pmol (exo⁻) Klenow DNA polymerase. The reaction was started by the addition of 40 pmol of the indicated deoxynucleotide and the PPi released was detected by the ELIDA. The loop-structure is designed to allow the addition of an extra A at the 3'-end during the PCR reaction, since some thermostable DNA polymerases, such as Taq DNA polymerase, show terminal transferase activity and add an extra non-template dependent A at the 3'-end; and FIG. 8 shows a schematic drawing of the set-up using a primer hybridised to a DNA-fragment immobilised onto a streptavidin-coated capillary.

EXAMPLE 1

Materials and Methods

Synthesis and Purification of Oligonucleotides

The oligonucleotides E2PN (55-mer: 5'CGACGATCTGAGGTCATAGCTGTTTCCTGTGTGA-ACTGGCCGTCGTTTTACAACG3'), E3PN (35-mer: 5'GCTGGAATTCGTCAGACTGGCCGTCGTTTTACAA-C3'), NUSPT (5'CTAAAACGACGGCCAGT3'), RIT 203 (5'-AGCTTGGGTTCGAGGAGATCTTCCGGGTTACGG-CGGAAGATCTCCTCGAGG), RIT 204 (5'-AG-CTCCTCGAGGAGATCTTCCGCCGTAACCCGGAAG-ATCTCCTCGAACCCA), ROMO 205S (5'-CGAGGAGATCTTCCGGGTTACGGCG), RIT 28, RIT 29, and USP (Hultman, T., Murby, M., Ståhl, S., Hornes, E., and Uhlén, M. (1990) Nucleic Acids Res. 18, 5107–5112) were synthesised by phosphoramidite chemistry on an automated DNA synthesis apparatus (Gene Assembler Plus, Pharmacia Biotech, Uppsala, Sweden). Purification was performed on a fast protein liquid chromatography pepRPC 5/5 column (Pharmacia, Biotech, Uppsala, Sweden).

In Vitro Amplification and Template Preparation

PCT reactions were performed on the multilinker of plasmid PRIT 28 with 7.5 pmol of general primers, RIT 28 and RIT 29 according to Hultman et al. (Supra). The PCR products were immobilised onto streptavidin-coated super paramagnetic beads Dynabeads™ M280-Streptavidin, or M450-Streptavidin (Dynal A. S., Oslo, Norway). Production of single-stranded DNA and hybridisation to sequencing primers was carried out as described earlier (Nyren, P., Pettersson, B., and Uhlén, M. (1993) Anal. Biochem. 208, 171–175).

Real-time DNA Sequencing

The oligonucleotide E3PN and the above described PCR product were used as templates for real-time DNA sequencing. The oligonucleotide E3PN was immobilised onto streptavidin-coated super paramagnetic beads (Dynabeads™ M280-Streptavidin or M450-Streptavidin) as described above, and a primer was hybridised to the immobilised template. The immobilised DNA-fragments were incubated with either a modified T7 DNA polymerase (Sequenase 2.0; U.S. Biochemical, Cleveland, Ohio, USA), Klenow DNA polymerase (Pharmacia, Biotech, Uppsala, Sweden), or exonuclease deficient (exo–) Klenow DNA polymerase (Amersham, UK). The sequencing procedure was carried out by stepwise elongation of the primer strand upon sequential addition of the different deoxynucleoside triphosphates (Pharmacia, Biotech, Uppsala, Sweden). Washing of the immobilised DNA fragments between each nucleotide addition was performed in two steps: first with a buffer containing 10 mM Tris-HCl (pH 7.5), 0.25 M NaCl, 0.1% Tween 20, and then with 10 mM Tris-acetate (pH 7.5). The PPi released due to nucleotide incorporation was detected by the ELIDA (Nyrén, P. (1987) Anal. Biochem. 167, 235–238). The luminescence was measured using an LKB 1250 luminometer connected to a potentiometric recorder. The luminometer was calibrated to give a response of 10 mV for the internal light standard. The luminescence output was calibrated by the addition of a known amount of ATP or PPi. The standard assay volume was 0.2 ml and contained the following components: 0.1 M Tris-acetate (pH 7.75), 2 mM EDTA, 10 mM magnesium acetate, 0.1% bovine serum albumin, 1 mM dithiothreitol, 5 $\mu$M adenosine 5'-phosphosulfate (APS), 0.4 mg/ml polyvinylpyrrolidone (360 000), 100 $\mu$g/ml D-luciferin (BioOrbit, Finland), 4 $\mu$g/ml L-luciferin (BioOrbit, Finland), 0.3 U/ml ATP sulfurylase (ATP:sulfate adenylyl transferase; EC 2.7.7.4) (Sigma Chemical Co., St. Louis, Mo., USA), purified luciferase (Sigma Chemical Co., St. Louis, Mo., USA) in an amount giving a response of 200 mV for 0.1 $\mu$M ATP. One pmol of the immobilised DNA-fragment, and 3 pmol DNA polymerase were added to the solution described above. The sequencing reaction was started by adding 40 pmol of one of the nucleotides (Pharmacia, Biotech, Uppsala, Sweden). The reaction was carried out at room temperature. When the effect of dATP and dATP$\alpha$S on the luciferase reaction was studied both APS and ATP sulfurylase were omitted from the assay.

Semi-automated Solid-phase DNA Sequencing

The sequence data obtained from the real-time DNA-sequencing was confirmed by semi-automated solid-phase sequencing (Hultman, T., Bergh, S., Moks, T., and Uhlén, M. (1991) BioTechniques 10, 84–93).

Results

Principle of the Sequencing Method

The principle of the sequencing method is illustrated in FIG. 1. A specific DNA-fragment of interest is immobilised onto a solid support (e.g. by biotin/streptavidin coupling) and subsequently converted into single-stranded form. A sequencing primer is hybridised to the single-stranded DNA, and a repeated cycle of deoxynucleotide incubation and washing is performed. The synthesis of DNA is accompanied by release of PPi equal in molarity to that of the incorporated nucleotide. Thereby, real-time signals are obtained by the ELIDA only when complementary bases are incorporated. In the ELIDA the produced PPi is converted to ATP by ATP sulfurylase and the amount of ATP is then determined by the luciferase assay (FIG. 1). From the ELIDA results the sequence after the primer is deduced.

Effect of dATP and dATP$\alpha$S on the Luciferase System

We have observed that dATP interfered with the detection system of the luciferase luminescence assay described by Nyren et al (Supra). This interference is a major problem when the method is used to detect a single-base incorporation event. Several approaches to decrease this background activity were tested (data not shown) and among those the largest positive effect was achieved by replacing the natural dATP with dATP$\alpha$S. FIG. 2 shows the results of using dATP and dATP$\alpha$S during the luciferase assay. An addition of 0.1 nmol dATP induced an instantaneous increase in the light emission followed by a slow decrease until it reached a steady-state level. The steady-state level increase in light emission after adding dATP corresponds to 1–2% of the emission from an equivalent addition of ATP. This effect of dATP makes it impossible to start a sequencing reaction by adding dATP; the reaction must instead be started by addition of DNA polymerase. The signal-to-noise ratio will also become higher for dATP compared to the other nucleotides. On the other hand, addition of 8 nmol dATP$\alpha$S (80-fold higher amount than dATP) had only a minor effect on the luciferase (FIG. 2). From FIG. 2 it can be deduced that dATP$\alpha$S is less than 0.05% as effective as dATP as a substrate for luciferase.

According to these results there is therefor a great advantage to using dATP$\alpha$S instead of dATP, together with a DNA polymerase that accepts this nucleotide.

Solid-phase Technique

Several different parameters were optimised in a model system using two different synthetic DNA templates. To simplify sequencing of several bases, the DNA was immobilised on a solid-phase. Here we have used two types of streptavidin-coated super paramagnetic beads from Dynal: M280 and M450. Both types of beads have a high binding capacity. We found that the larger beads (M450) allow a faster washing procedure due to their higher sedimentation rate (data not shown). To eliminate blunt-end DNA polymerase activity (Clak, J. M. (1991) Gene, 104, 75–80), sequence primers annealing at least one base inside from the 3' end of the template were chosen. In FIG. 3, a single-base incorporation event is shown for two different concentrations of primer/template. The reactions were started by addition of the next correct base (dCTP) and the traces show the release of PPi during the incorporation of the base. No release of PPi was observed if a non-complementary base was added (data not shown). In the subsequent experiments 1 pmol of primer/template was used and the relevant signal difference was recorded (FIG. 3). Both the initial rate and the extent of PPi formed in the ELIDA are proportional to the DNA concentration within a broad interval (Hultman et al., supra). The upper limit for the assay is 200 pmol PPi formed (1 $\mu$M) (Nyrén, P., and Lundin, A. (1985) Anal. Biochem. 151, 504–509). The lower limit is mainly determined by the volume used, and by contamination of PPi and ATP in the different solutions.

Effect of DNA Polymerase Concentration

In the next series of experiments the effect of polymerase concentration on the sequencing procedure was studied. We found that it was important to use an excess of polymerase over primer/template to be sure that all free 3' ends were extended. At lower polymerase concentrations biphasic kinetics (a fast phase followed by a slower phase) was observed (data not shown). The amplitude of the fast phase is stoichiometric with the amount of enzyme present, and the slow phase is the same as the rate of steady-state incorporation. The rate limiting steps for the slow phase are the dissociation of the polymerase from the extended primer/template and the subsequent binding to a not-extended primer/template. The incorporation rate as a function of nucleotide concentration was also studied. We observed a Km, for one base incorporation, of 0.2 and 0.4 $\mu$M for Klenow and Sequenase 2.0, respectively (not shown). The latter results are in accordance with data from the literature (Van Draanen, N. A., Tucker, S. C., Boyd, F. L., Trotter, B. W., and Reardon, J. E. (1992) J. Biol. Chem. 267, 25019–25024).

Real-time DNA Sequencing

Different synthetic templates as well as a PCR product were sequenced in order to investigate the feasibility of the new approach. Extension of one base on three different primer/templates are shown in FIG. 4. Both the rate and extent (slope and height of the signals) of nucleotide incorporation were similar for all three types of templates tested. In FIG. 5 realtime DNA sequencing of 15 bases of a 291-base-long single-stranded PCR product is shown. The sequencing procedure was started by addition of dATP$\alpha$S. No PPi release due to base incorporation was detected in the ELIDA. The small signal observed is due to PPi contamination in the nucleotide solution. After a washing step, dGTP was added; a signal corresponding to incorporation of one residue was observed. The next base added was dCTP; a signal corresponding to incorporation of two identical residues was now detected. The subsequent addition of dTTP gave no signal. Thereafter, dATP$\alpha$S was added again. This time the incorporation of two identical residues was noted. The latter detected incorporation confirmed earlier observations (Vosberg, H. P., and Eckstein, f. (1977) Biochemistry 16, 3633–3640) that dATPαS is efficiently incorporated into the primer/template by Klenow polymerase. A signal corresponding to incorporation of one residue was obtained after the next addition which was dGTP. By continuing this cyclic procedure further information about the sequence was obtained. It is important to note that enough nucleotides must be added to allow longer extensions when there is a stretch of identical residues. The sequencing procedures were repeated several times on the same template with the same result. The decrease in signal due to loss and aggregation of beads during the washing procedure (measured by the decrease in optical density) has been compensated for in FIG. 5. The loss was lower for the M450 beads than for the M280. The obtained sequence was confirmed by semi-automated solid-phase Sanger sequencing (data not shown).

EXAMPLE 2

Materials and Methods
Construction of the Hairpin Vector pRIT 28 HP and Preparation of Template The oligonucleotides RIT 203, and RIT 204 (prepared as described in Example 1) were hybridised, and ligated to HindIII (Pharmacia, Biotech, Uppsala, Sweden) pre-restricted plasmid pRIT 28 (Hultman et al. 1990, supra). PCR reaction was performed on the multilinker of plasmid pRIT 28 HP with 7.5 pmol of primer pairs, RIT 29/ROMO 205S, 200 µM dNTP, 20 mM Tris-HCl pH 8.7, 2 mM MgCl$_2$, 0.1% Tween 20 and 1 unit AmpliTaq DNA Polymerase (Perkin Elmer, Cetus, Emeryville, USA) making up a final volume of 50 µl. The temperature profile included a 15 seconds denaturation step at 95° C. and a 90 seconds annealing/extension step at 72° C. These steps were repeated 35 times with a GeneAmp PCR System, 9600 (Perkin Elmer, Emeryville, USA). The biotinylated PCR products were immobilised onto streptavidin-coated superparamagnetic beads (Dynabeads™ M280-Streptavidin, from Dynal A. S., Oslo, Norway). The beads were used as described by the manufacturer (Dynal A S, Oslo, Noway). Single-stranded DNA was obtained by removing the supernatant after incubation of the immobilised PCR product in 0.1 M NaOH for 5 minutes. The immobilised single-stranded DNA was washed first with 1×TE (Tris-HCl 10 mM, 1 mM EDTA, pH 7.5) and was hybridised at 65° C. for 5 minutes in 20 mM Tris-HCl pH 7.5, 8 mM MgCl$_2$ to make a loop-structure for real-time DNA sequencing.

Real-time DNA Sequencing on Loop-structure

The prepared loop-structure immobilised on superparamagnetic beads was incubated with (exo$^-$) Klenow DNA polymerase. The sequencing procedure was carried out as described in Example 1.

Results

The principle of generating a loop-structure as a template for use in real-time sequencing is shown in FIG. 6. This method involves the use of only one biotinylated primer which is used to immobilise the hybridised product of amplification. The non-biotinylated strand is removed allowing formation of the loop-structure by hybridisation. The results of using the immobilised loop-structure are shown in FIG. 7 for 12 subsequent sequencing cycles. By this method, the sequence of the first 10 bases adjacent to the loop-primer could be determined.

Sequencing may be performed by using a capillary as a solid support and a schematic representation for the set-up using an immobilised DNA-fragment with hybridised primer (as in Example 1) is shown in FIG. 8. A similar set-up may be used for immobilised DNA-fragment with loop-primer.

What is claimed is:

1. A method of identifying a base at a target position in a single-stranded sample DNA sequence wherein an extension primer, which hybridizes to the sample DNA immediately adjacent to the target position is provided and the sample DNA and extension primer are subjected to a polymerase reaction in the presence of a deoxynucleotide or dideoxynucleotide whereby the deoxynucleotide or dideoxynucleotide will only become incorporated and release pyrophosphate (PPi) if it is complementary to the base in the target position, and whereby any release of PPi is detected enzymically in the same step as the polymerase reaction, different deoxynucleotides or dideoxynucleotides being added either to separate aliquots of sample-primer mixture or successively to the same sample-primer mixture and subjected to the polymerase reaction to indicate which deoxynucleotide or dideoxynucleotide is incorporated, characterized in that, the PPi-detection enzyme(s) are included in the polymerase reaction step and in that in place of deoxy- or dideoxy adenosine triphosphate (ATP) a dATP or ddATP analogue is used which is capable of acting as a substrate for a polymerase but incapable of acting as a substrate for a said PPi-detection enzyme and wherein release of PPi is indicative of incorporation of deoxynucleotide or dideoxynucleotide and the identification of a base complementary thereto.

2. A method as claimed in claim 1, wherein the release of PPi is detected by means of a luciferase-luciferin-based reaction.

3. A method as claimed in claim 2, wherein PPi release is detected using the Enzymatic Luminometric Inorganic Pyrophosphate Detection Assay (ELIDA).

4. A method as claimed in claim 1, wherein the dATP or ddATP analogue is deoxyadenosine α-thiotriphosphate (dATPαS).

5. A method as claimed in claim 1, further comprising the use of the α-thio analogues of dCTP, dGTP and dTTP.

6. A method as claimed in claim 1, wherein the sample DNA is immobilised or provided with means for attachment to a solid support.

7. A method as claimed in claim 1, wherein the sample DNA is first amplified.

8. A method as claimed in claim 1, wherein the extension primer contains a loop and wherein the extension primer anneals back on itself and the 3' end of the sample DNA.

9. A method as claimed in claim 1, wherein the sample DNA is subjected to amplification;

the amplified DNA is immobilised and then subjected to strand separation, the non-immobilised strand being removed and an extension primer, which hybridises to the immobilised DNA immediately adjacent to the target position, is provided; each of four aliquots of the immobilised single stranded DNA is then subjected to a polymerase reaction in the presence of a dideoxynucleotide, each aliquot using a different dideoxynucleotide whereby only the dideoxynucleotide complementary to the base in the target position becomes incorporated; the four aliquots are then subjected to extension in the presence of all four deoxynucleotides, whereby in each aliquot the DNA which has not reacted with the dideoxynucleotide is extended to form double stranded DNA while the dideoxy-blocked DNA remains as single stranded DNA; followed by identification of the double stranded and/or single stranded DNA to indicate which dideoxynucleotide was incorporated and hence which base was present in the target position.

10. A method as claimed in claim 1, wherein the polymerase in the polymerase reaction step is exonuclease deficient (exo⁻).

11. A method as claimed in claim 1, for use with a multiplicity of sample DNA sequences, wherein said DNA sequences are arranged in assay format on a solid surface.

* * * * *

UNITED STATES PATENT AND TRADEMARK OFFICE
CERTIFICATE OF CORRECTION

PATENT NO. : 6,210,891 B1 Page 1 of 2
DATED : April 3, 2001
INVENTOR(S) : Nyren et al.

It is certified that error appears in the above-identified patent and that said Letters Patent is hereby corrected as shown below:

Title Page,
Item [56], References Cited, FOREIGN PATENT DOCUMENTS: "WO 93/233563 11/1993 (WO)" should read -- WO 93/23563 11/1993 (WO) --
Insert the following Foreign Patent References:
-- German Patent DE 19602662, August 7, 1997
German Patent DE 3546374, July 2, 1987
European Patent EP 0054676, June 30, 1982
European Patent Application Publication: 0 223 618, May 27, 1987
European Patent EP 0566140, October 20, 1993
European Patent EP 0756637, February 5, 1997
European Patent EP 0701625, March 20, 1996
French Patent FR 2674254, September 25, 1992
International Application Publication No. WO 90/04649, May 3, 1990
International Application Publication No. WO 91/05065, April 18, 1991
International Application Publication No. WO 92/06219, April 16, 1992
International Application Publication No. WO 92/16654, October 1, 1992
International Application Publication No. WO 93/23415, November 25, 1993
International Application Publication No. WO 96/10640, April 11, 1996
International Application Publication No. WO 96/29424, September 26, 1996
International Application Publication No. WO 98/55653, December 10, 1998
International Application Publication No. WO 99/05315, February 4, 1999
International Application Publication No. WO 00/11222, March 2, 2000 --
Item [75], Inventor(s): "Skarpnäack" should read -- Skarpnäck --

Column 3,
First reaction,
"ATP sulphurylase

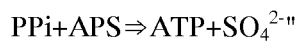
$PPi + APS \Rightarrow ATP + SO_4^{2-}$"

should read

-- ATP sulphurylase
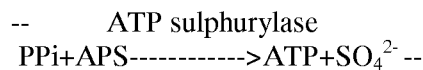
$PPi + APS \text{------------}> ATP + SO_4^{2-}$ --

UNITED STATES PATENT AND TRADEMARK OFFICE
CERTIFICATE OF CORRECTION

PATENT NO. : 6,210,891 B1
DATED : April 3, 2001
INVENTOR(S) : Nyren et al.

It is certified that error appears in the above-identified patent and that said Letters Patent is hereby corrected as shown below:

Column 3 (con't),
Second reaction,
"luciferase $$ATP + luciferin + O_2 \Rightarrow AMP + PPi + oxyluciferin + CO_2 + hv"$$

should read

--                 luciferase
$ATP + luciferin + O_2 ------> AMP + PPi + oxyluciferin + CO_2 + hv$ --

Column 7,
Line 12, "3'-thereto" should read -- 3'- thereto --

Column 12,
Line 34, "PRIT 28" should read -- pRIT 28 --

Signed and Sealed this

Nineteenth Day of November, 2002

*Attest:*

JAMES E. ROGAN
*Attesting Officer*     *Director of the United States Patent and Trademark Office*